United States Patent [19]

Leber

[11] 4,185,052

[45] Jan. 22, 1980

[54] PROCESS FOR THIOPHOSPHORIC ACID DERIVATIVES

[75] Inventor: Jean-Pierre Leber, Basel, Switzerland

[73] Assignee: Sandoz Ltd., Basel, Switzerland

[21] Appl. No.: 914,515

[22] Filed: Jun. 12, 1978

Related U.S. Application Data

[63] Continuation-in-part of Ser. No. 831,015, Sep. 6, 1977, abandoned.

[30] Foreign Application Priority Data

Sep. 8, 1976 [CH] Switzerland ............ 11387/76
Sep. 8, 1976 [CH] Switzerland ............ 11389/76

[51] Int. Cl.² ............................................. C07F 9/206
[52] U.S. Cl. ...................................... 260/972; 260/941
[58] Field of Search .................................... 260/972

[56] References Cited

U.S. PATENT DOCUMENTS

3,649,716   3/1972   Leber .................. 260/972 X

Primary Examiner—Anton H. Sutto

Attorney, Agent, or Firm—Gerald D. Sharkin; Richard E. Vila

[57] ABSTRACT

The present invention relates to a novel process for the production of thiophosphoric acid derivatives of the formula $$\begin{array}{c} Y_1 \\ \diagdown \\ Y_2 \diagup \end{array} \overset{S}{\underset{\|}{P}} - O \diagdown \underset{CH_3}{\overset{}{C}} = C \diagup \overset{X}{\diagdown} COOR_1$$

wherein
  $R_1$ is $C_1$-$C_5$ alkyl
  X is H, Cl or Br
  $Y_1$ is $C_1$-$C_5$ alkoxy, Cl or Br and
  $Y_2$ is Cl or Br and
  the —$CH_3$ and —$COOR_1$ radicals are Cis one to another in the crotonic acid moiety.

The compounds of formula I are useful intermediates in the production of known insecticides.

7 Claims, No Drawings

PROCESS FOR THIOPHOSPHORIC ACID DERIVATIVES

This application is a continuation-in-part of application Ser. No. 831,015, filed Sept. 6, 1977, now abandoned.

The present invention relates to a process for the production of thiophosphoric acid derivatives.

Accordingly the present invention provides a process for the production of a compound of formula I

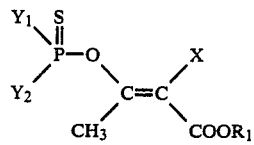

wherein
$R_1$ is $C_1$-$C_5$ alkyl
X is H, Cl or Br
$Y_1$ is $C_1$-$C_5$ alkoxy, Cl or Br and
$Y_2$ is Cl or Br and
the —$CH_3$ and —$COOR_1$ radicals are Cis one to another in the crotonic acid moiety,
which comprises condensing a compound of formula II

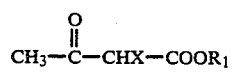

wherein X and $R_1$ are as defined above with a compound of formula III

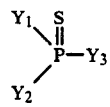

wherein
$Y_1$ and $Y_2$ are as defined above and
$Y_3$ is Cl or Br
in an aqueous organic two phase system, in the presence of an alkali and a catalytic amount of a phase transfer catalyst.

Appropriate phase transfer catalysts are quaternary ammonium and quaternary phosphonium compounds as well as crown ethers. Preferred are quaternary ammonium and quaternary phosphonium compounds.

Preferred quaternary ammonium salts are tetra($C_1$-$C_{20}$)alkyl and benzyl tri($C_1$-$C_{20}$)alkyl ammonium salts such as the sulphate, phosphate, benzene sulphonate, toluene sulphonate and particularly the hydrohalide salts such as the chloride bromide and iodide.

Specific examples of quaternary ammonium salts are benzyltrimethyl ammonium bromide and hydroxide, benzyltriethyl ammonium bromide and chloride, benzyltributylammonium bromide, cetyltrimethyl ammonium bromide, methyltributyl ammonium iodide, tetraethyl ammonium chloride, bromide, iodide and hydroxide, tricaprylylmethyl ammonium chloride, centrimide (trade mark) and tetrabutyl ammonium chloride, bromide, iodide, hydrogen sulphate and hydroxide.

Preferred quaternary phosphonium salts are tetraphenyl, triphenyl($C_1$-$C_{20}$)alkyl and tetra($C_1$-$C_{20}$) alkyl phosphonium salts such as the halide salts.

Specific examples of quaternary phosphonium salts are benzyltriphenyl phosphonium chloride and tetraphenylphosphonium bromide and chloride.

Examples of crown ethers are 18-crown-6, 15-crown-5 and 12-crown-4.

Preferred alkalis are sodium or potassium hydroxide especially when present in the aqueous phase in amounts of 10–30% by weight especially 15 to 25% by weight.

The organic phase may comprise any appropriate inert water immiscible solvent such as halogenated hydrocarbons, e.g. 0-dichloro benzene, methylene dichloride, 1,2-dichloroethylene, trichloroethylene, tetrachloroethylene and chloroform.

The reaction is preferably effected at a temperature in the range −10° to +25° C. particularly in the range −5° to +5° C.

The process enables the stereospecific synthesis of compounds of formula I in high yield and in a high state of purity.

The compounds of formula I are useful known intermediates in the production of compounds of formula IV

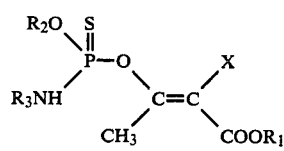

wherein
$R_1$ and X are as defined above
$R_2$ is $C_1$-$C_5$ alkyl and
$R_3$ is $C_1$-$C_5$ alkyl and
the —$CH_3$ and —$COOR_1$ radicals are Cis one to another in the crotonic acid moiety.

The compounds of formula IV may be produced (a) by condensing a compound of formula Ia

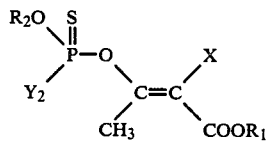

wherein
$R_1$, X, $R_2$ and $Y_2$ are as defined above, and
the —$CH_3$ and —$COOR_1$ radicals are Cis one to another in the crotonic acid moiety,
with a compound of formula V

wherein $R_3$ is as defined above, or (b) by condensing a compound of formula Ib

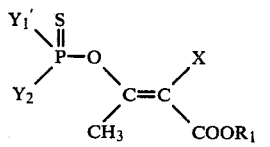

wherein
$Y_2$, X and $R_1$ are as defined above and
$Y_1'$ is Cl or Br and the —CH₃ and COOR₁ radicals are Cis one to another in the crotonic acid moiety,
with a compound of formula VI $$R_2OM \qquad VI$$

wherein
R₂ is as defined above and
M is H or an alkali metal or ammonium cation
to produce a compound of formula Ia and then following the procedure of process (a) above.

The compounds of formula IV are known useful insecticides.

The invention is illustrated by the following Examples wherein temperatures are expressed in °C. and parts are by weight.

EXAMPLE 1 cis-0-(1-carboisopropoxy-1-propen-2-yl)-thionophosphoric acid dichloride 144.2 g (1 mol) of acetoacetic acid isopropylester are added at 0° to a solution of 169.4 g (1 mol) of thiophosphoryl chloride in 1.2 l of chloroform, and 22.8 g (0.1 mol) of benzyltriethylammonium chloride are subsequently added. A solution of 40 g of sodium hydroxide in 0.2 l of water is added with vigorous stirring to the mixture which is kept at 0° and stirring is continued for 15 minutes at 0°. The chloroform phase is allowed to settle, then partitioned off in a separating funnel, washed with 0.2 l of ice-cold water and dried over anhydrous sodium sulphate. After evaporating off the solvent in a vacuum on a rotary evaporator, the residue is subjected to high vacuum at $10^{-4}$ torr (bath temperature 50°).

The trans isomer could not be detected in the residue. The purity is tested by thin-layer chromatography on silica gel plates, with n-hexane/acetone (4:1) as the elvant, and the samples rendered visible by spraying with alkaline permanganate solution. The Rf values of the title product and starting materials are as follows:
cis-0-(1-carboisopropoxy-1-propen-2-yl)-thionophosphoric acid dichloride, $R_f=0.66$
0,0-bis-(1-carboisopropoxy-1-propen-2yl)-thionophosphoric acid chloride $R_f=0.52$
acetoacetic acid isopropylester $R_f=0.32$ If an oily residue is obtained after the solvent is evaporated off, it may be filtered through a filtering aid such as Hyflo. The title compound which adheres to the Hyflo may be washed out by treatment with petroleum ether in which it is soluble.

EXAMPLE 2 cis-0-(1-carboisopropoxy-1-propen-2yl)-thionophosphoric acid dichloride 195 g (1.15 mols) of thionophosphoryl chloride are dissolved in 1.2 l of chloroform, 22.8 g (0.1 mols) of benzyltriethylammonium chloride are added with good stirring to the solution which is kept constantly at −5°, and 240 ml of 20% aqueous caustic soda (1.2 mols) are added over the course of 10 minutes in a slightly exothermic reaction. Immediately afterwards, 144.17 g (1 mol) of acetoacetic acid isopropylester are added dropwise at −5° over the course of 30 minutes. Stirring takes place for another ¼ hour at 0° and the process is completed as described in Example 1. No trans compound can be detected.

The cis-0-(1-carboisopropoxy-1-propen-2-yl)-thionophosphoric acid dichloride produced in Examples 1 and 2 may be distilled if desired in a high vacuum at 43°/5×10⁻⁵mm; $n_D^{20}=1.5078$.

The cis and trans title compounds are distinguished by the NMR signals, primarily from the substituents on the vinylic double compound.

NMR (δ, ppm in CDCl₃)
cis-0-(1-carboisopropoxy-1-propen-2-yl)-thionophosphoric acid dichloride =CH 5.9 multiplett; CH₃C= 2.52 ppm trans-0-(1-carboisopropoxy-1-propen-2-yl)-thionophosphoric acid dichloride =CH 5.62 multiplett; CH₃C= 2.20 ppm.

EXAMPLE 3 cis-O-(1-carboisopropoxy-1-propen-2-yl)-O-methyl-thionophosphoric acid chloride 165 g (1 mol) of O-methyl-thionophosphoric acid dichloride are dissolved in 500 ml of chloroform. 57 g (0.25 mols) of benzyltriethylammonium chloride are added with stirring at 0° and 144 g (1 mol) of acetoacetic acid isopropylester are subsequently added with vigorous stirring at 0°. 1 mol of 20% aqueous caustic soda is subsequently added dropwise at the same temperature over the course of ½ hour, and the mixture is stirred for another ¼ hour at 0°. The chloroform phase is now separated off and washed for a short time in a separating funnel with 0.2 l of ice-cold water. After drying over sodium sulphate and evaporating off the solvent in a rotary evaporator under vacuum, the title compound is obtained. The purity of the product may be tested by gas chromatography.

The test with gas chromatography showed practically pure cis-O-(1-carboisopropoxy-1-propen-2yl)-O-methyl-thionophosphoric acid chloride.

The test for purity may also be effected by thin-layer chromatography on silica gel plates, with n-hexane-/acetone (4:1) as the eluant, the samples being visible by spraying with alkaline permanganate solution.

The title compound may be distilled in a high vacuum.
Bp. 67°/0.05 mm, $n_D^{20}=1.4926$.

EXAMPLE 4 cis-O-(1-carboisopropoxy-1-propen-2-yl)-O-methyl-N-ethyl-thionophosphoric acid esteramide 405 ml (10 mols) of anhydrous methanol are cooled to about −5°. 194.8 g (1.15 mols) of thionophosphoric acid chloride are then added and the mixture stirred for about 10 minutes at 10°. 1.2 l of ice-cold water are added, the mixture is decanted from the O-methyl-thionophosphoric acid chloride which settles on the bottom, and washed twice, each time with 120 ml of ice-cold water. The O-methyl-thionophosphoric acid dichloride thus obtained [165 g (1 mol)] is dissolved in 500 ml of chloroform. 57 g (0.25 mols) of benzyltriethylammonium chloride are then added with stirring at 0°, and 144 g (1 mol) of acetoacetic acid isopropylester are subsequently added with vigorous stirring at 0°. 1 mol of 20% aqueous caustic soda is subsequently added dropwise at the same temperature over the course of ½ hour, and this is further stirred at 0° for ¼ hour. Immediately afterwards, 129 g (2 mols) of ethylamine are added in the form of a 70% aqueous solution at −5° over the course of ¼ hour. The mixture is stirred for another ¼ hour at 0°, the chloroform phase is then partitioned off in a separating funnel and washed once with 0.2 l of water. After drying over sodium sulphate, the solvent is evaporated off on a rotary evaporator under a water jet vacuum. The residue is subjected to a temperature of 70° under a high vacuum ($10^{-4}$ torr) for ½ hour. It is then treated with petroleum ether (boiling range 100°-125°). The ether phase which contains the title compound is evaporated on a rotary evaporator under a water jet vacuum, and subsequently subjected to high vacuum for ½ hour.

The title compound is obtained in at least 90% purity. It can be distilled at 87°-89°/5 $10^{-3}$ torr. $n_D^{20}=1.495$.

EXAMPLE 5 cis-O-(1-carboisopropoxy-1-propen-2-yl)-thionophosphoric acid dichloride 97.5 g (0.57 mol) of thionophosphorylchloride are dissolved in 0.6 L of chloroform. 17.8 g (0.05 mol) of benzyltributylammonium bromide are added with stirring, the solution being cooled and maintained at −5° C., and 120 ml of 20% aqueous caustic soda (0.6 mol) are added over the course of 10 minutes in a slightly exothermic reaction. Immediately afterwards, 72.1 g (0.5 mol) of acetoacetic acid isopropyl ester are added dropwise. Stirring is carried out at 0° C. for 15 minutes and isolation is carried out in accordance with the procedure described in Example 1.

A product identical to that obtained in Example 2, and free from any detectable trans isomer, is obtained.

EXAMPLE 6 cis-O-(1-carboisopropoxy-1-propen-2-yl)-O-methyl-N-ethyl-thionophosphoric acid ester amide O-methyl-thionophosphoric acid chloride (165 g; 1 mol), obtained as described in Example 4, is dissolved in 500 ml of chloroform. The solution is cooled to 0° C. and there is added, with stirring, 144 g (1 mol) of acetoacetic acid isopropyl ester followed by 85 g (0.25 mol) of tetrabutylammonium hydrogen sulphate. Finally, with vigorous stirring at 0° C., 1.5 mol of a 20% aqueous solution of sodium hydroxide is added over ½ an hour.

The mixture is further stirred for ½ hour at 0° C., followed by quick cooling to −5° C. and immediate subsequent addition, whilst maintaining the temperature at −5° C., of 129 g (2 mols) of ethylamine as a 70% aqueous solution. Further stirring for ½ hour at 0° C. then takes place, followed by isolation as described in Example 4. A product identical with that of Example 4 is obtained.

EXAMPLE 7 cis-O-(1-chloro-1-carboisopropoxy-1-propen-2-yl)-thionophosphoric acid dichloride To a solution of 56 g (0.33 mol) thionophosphoryl chloride and 53.6 g (0.3 mol) α-chloroacetoacetic acid isopropyl ester in 0.4 L chloroform is added, at 0° C., 6.8 g (0.03 mol) benzyltriethylammonium chloride, whereafter, over a period of 10 minutes, 72 ml of a 20% aqueous sodium hydroxide (0.36 mol) solution is added with vigorous stirring (slight exothermic reaction). Stirring is continued for a further 15 mins at 0° C. The chloroform phase is then separated off and washed in a separating funnel with 0.2 L of ice-cold water followed by drying over anhydrous sodium sulphate. After evaporation of the solvent in a rotary evaporator, under vacuum, the residue is dried again under vacuum ($10^{-4}$ torr) at 50° C. The title compound, uncontaminated with trans isomer, can be distilled at 52° C./$10^{-3}$ torr, $n_D^{20}$ 1,482. This cis compound is distinguished by the NMR signals, particularly by the position of the CH$_3$C= doublet at 2.65 ppm (I=6 cps). With the trans compound this doublet is at 2.4 ppm.

EXAMPLE 8 cis-O-(1-carboisopropoxy-1-propen-2-yl)-thionophosphoric acid dichloride

To a solution of 33.9 g (0.2 mol) thionophosphoryl chloride in 0.25 L chloroform is added, at 0° C., 28.8 g (0.2 mol) acetoacetic acid isopropyl ester followed by 8.4 g of tetraphenylphosphonium bromide [(C$_6$H$_5$)$_4$P$^\oplus$Br$^\ominus$]. This is followed by an addition of a solution of 8.0 g sodium hydroxide in 40 ml of water, with vigorous stirring and maintaining the temperature at 0° C. Stirring then continues for 15 mins (at 0° C.). The chloroform layer is then separated and washed with 40 ml of water, dried over anhydrous sodium sulphate, evaporated and the semi-solid residue extracted with ether. 50 g of the title compound are obtained in practically pure form. It has the same properties as the product of Example 2.

EXAMPLE 9 cis-O-(1-carboisopropoxy-1-propen-2-yl)-thionophosphoric acid dichloride

To a solution of 1.69 g (0.01 mol) thionophosphoryl chloride in 25 ml of chloroform, there is added at 0° C., 1.44 g (0.01 mol) acetoacetic acid isopropyl ester and 5,3 g of the crown ether, 18-crown 6, of formula

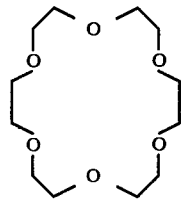

There is then added over 15 mins at 0° C. a solution of potassium hydroxide in 2 ml water. After a further 15 mins stirring, the phases are separated, the organic phase being washed with water, dried over Na$_2$SO$_4$ and evaporated. The residue is then extracted with ether to separate the catalyst. The residue (2.4 g) from the ether is then subjected to thin-layer chromatography yielding a single spot of the title compound adjacent a trace spot of unreacted acetic acid ester.

EXAMPLE 10

The procedure of Example 9 is repeated but instead of the 18-crown-6, there is employed 7.2 g of the crown ether dibenzo-18-crown-6, of formula

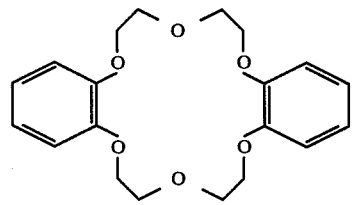

2.3 g of the product are obtained which is subjected to thin-layer chromatography giving a principal spot of the title compound of Example 9 at the side of a trace spot of unreacted acetic acid ester, together with a very light spot of the trans-isomer (Rf=0.48) amounting to less than 5% of the product.

I claim:

1. A process for the production of a compound of formula I

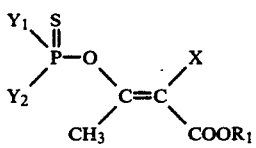

wherein
- $R_1$ is $C_1-C_5$ alkyl
- X is H, Cl or Br
- $Y_1$ is $C_1-C_5$ alkoxy, Cl or Br and
- $Y_2$ is Cl or Br and
- the —$CH_3$ and —$COOR_1$ radicals are Cis one to another in the crotonic acid moiety, which comprises condensing a compound of formula II

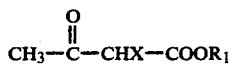

wherein X and $R_1$ are as defined above with a compound of formula III

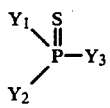

wherein
- $Y_1$ and $Y_2$ are as defined above and
- $Y_3$ is Cl or Br in an aqueous organic two phase system, in the presence of an alkali and a catalytic amount of a phase transfer catalyst.

2. A process according to claim 1 wherein the phase transfer catalyst is a quaternary ammonium or quaternary phosphonium catalyst.

3. A process according to claim 2 wherein the phase transfer catalyst is a tetra($C_1-C_{20}$)alkyl or benzyltri($C_1-C_{20}$)alkyl quaternary ammonium salt.

4. A process according to claim 1 when effected at a temperature in the range $-10°$ to $+25°$ C.

5. A process according to claim 2 when effected at a temperature of from $-10°$ to $+25°$ C.

6. A process according to claim 3 when effected at a temperature of from $-10°$ to $+25°$ C.

7. A process according to claim 6 in which the phase transfer catalyst is benzyltriethylammonium chloride.

* * * * *